United States Patent [19]
Etess et al.

[11] 3,967,933
[45] July 6, 1976

[54] DUAL CHANNEL NITROGEN OXIDES ANALYZER

[75] Inventors: Edward Etess, La Jolla; Allan L. Budd, San Diego, both of Calif.

[73] Assignee: Monitor Labs, Inc., San Diego, Calif.

[22] Filed: May 23, 1974

[21] Appl. No.: 472,698

[52] U.S. Cl. .......................... 23/232 E; 23/232 R; 23/254 R; 23/254 E; 23/255 R; 23/255 E; 250/361
[51] Int. Cl.² ........................................ G01N 33/00
[58] Field of Search .......... 23/232 R, 232 E, 254 R, 23/254 E, 255 R, 255 E; 250/361 C

[56] References Cited
UNITED STATES PATENTS

| | | | |
|---|---|---|---|
| 2,394,129 | 2/1946 | West | 356/206 |
| 2,449,067 | 9/1948 | Guillemin, Jr. | 23/232 R X |
| 3,046,098 | 7/1962 | Brasseur et al. | 23/232 R X |
| 3,224,838 | 12/1965 | Evans et al. | 23/254 E X |
| 3,300,282 | 1/1967 | Risk et al. | 23/232 R |
| 3,407,124 | 10/1968 | Pasik | 23/232 R X |
| 3,447,906 | 6/1969 | Zimmerli | 23/253 R |
| 3,528,779 | 9/1970 | Fontijn | 23/254 E X |
| 3,730,686 | 5/1973 | Breitenbach et al. | 23/232 R |
| 3,734,691 | 5/1973 | Kukla et al. | 23/254 R X |
| 3,882,028 | 5/1975 | Zolner | 250/361 C |

*Primary Examiner*—Joseph Scovronek
*Attorney, Agent, or Firm*—Morris Liss

[57] ABSTRACT

Sample air is divided into two paths. One path leads through a thermal converter where ambient $NO_2$ is changed into NO. The other path passes through equivalent tubing to keep the air samples synchronized. Both samples then go to separate cells where each combines with ozone. The resulting chemical reaction produces light, chemiluminescence, which is measured by separate photo-multiplier tubes. Electronic circuits translate the results into simultaneous readings of $NO_x$ and NO concentrations. A difference amplifier subtracts the NO from the $NO_x$ to give a continuous $NO_2$ value.

10 Claims, 5 Drawing Figures

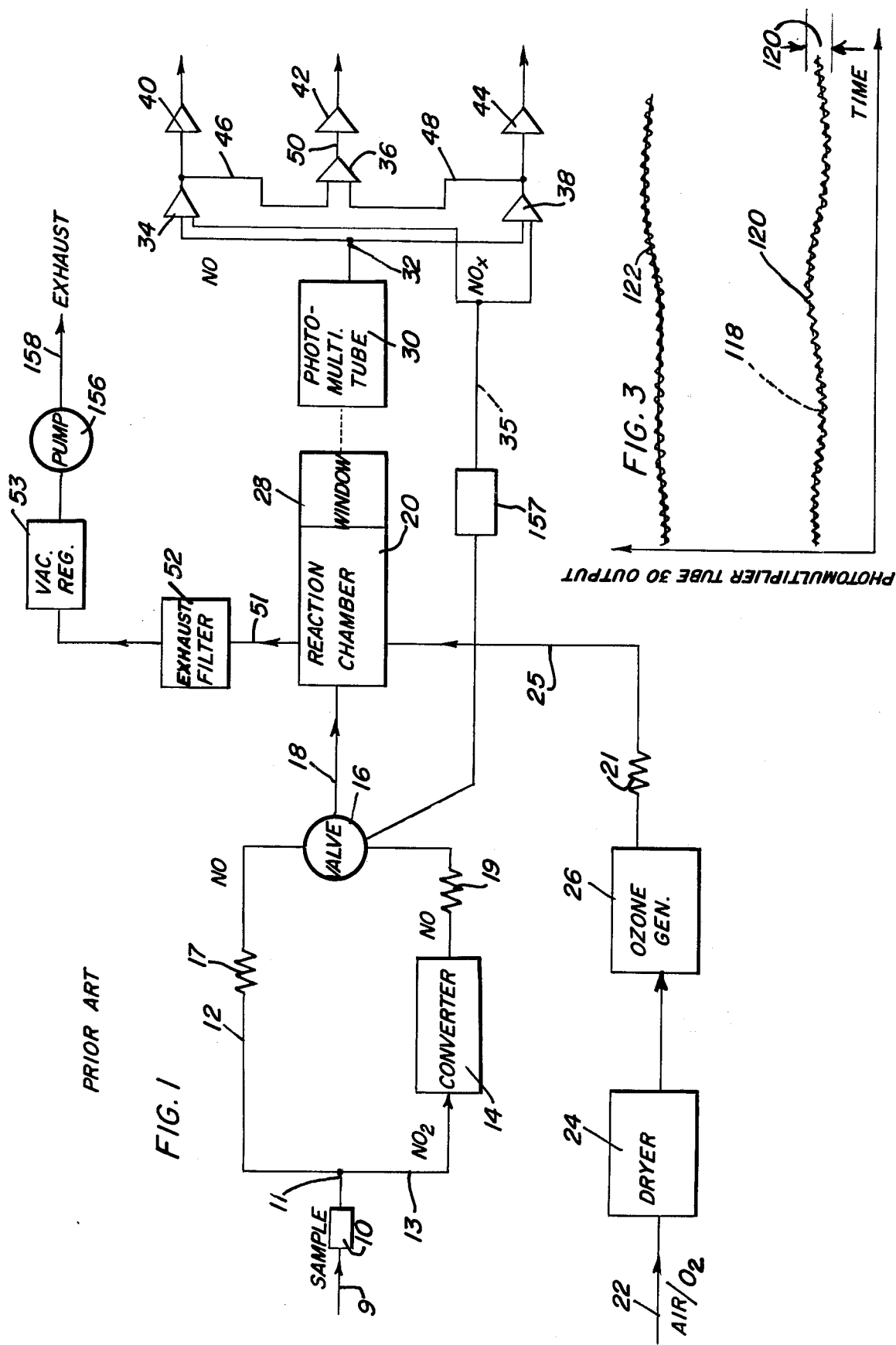

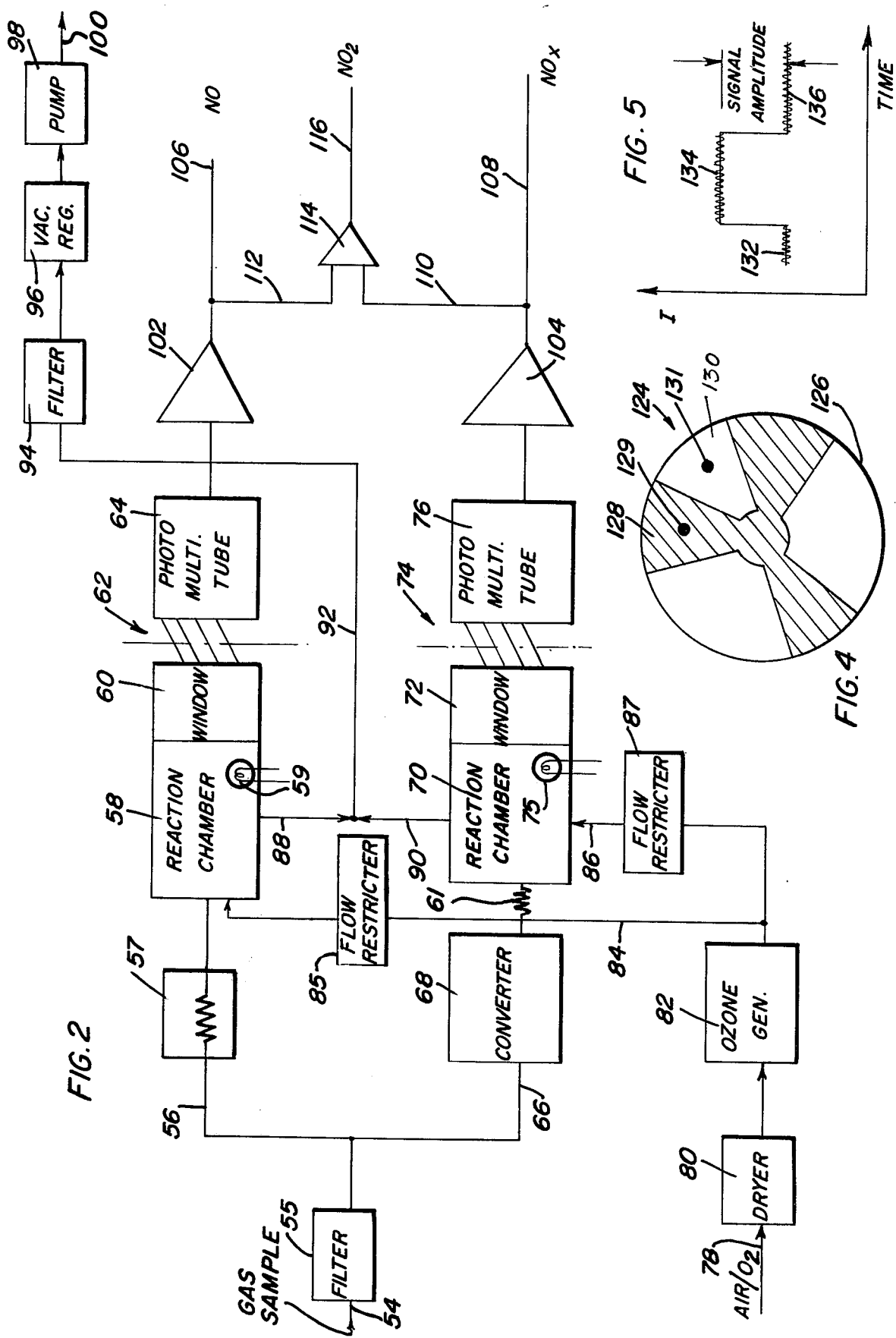

3,967,933

DUAL CHANNEL NITROGEN OXIDES ANALYZER

FIELD OF THE INVENTION

The present invention relates to gas analyzers, and more particularly to an analyzer for analyzing the compounds of gases, such as oxides of nitrogen by utilizing a chemical reaction which produces light by chemiluminescence.

BRIEF DESCRIPTION OF THE PRIOR ART

Previous related instruments have used a single channel and a solenoid valve to alternately send compounds of a gas, such as NO and $NO_x$ to a reaction cell and measuring circuit. The problem with such prior art apparatus is that there is a time lag between each measurement of NO and $NO_x$ — typically about 1 minute. So when $NO_2$ is found by subtracting the two readings, the anaylzer is actually comparing the ambient NO with the $NO_x$ that was present one minute earlier. This "skew" error will be large during conditions of changing ambient concentrations. Such changes occur in high vehicle traffic areas or downwind from emission sources. The error is large enough in some cases to invalidate critical data needed for use in support of (or defence against) an air regulation citation. Not only does time-lag reduce validity, it can produce obviously faulty negative $NO_2$ readings. This can happen when some temporary NO source — such as a passing truck — is present while the instrument is operating during the NO cycle. When this very high NO reading is subtracted from a normal $NO_x$ reading, taken one minute before, a negative value for $NO_2$ can result.

Another problem has reduced the validity of analyzer data for compounds of gases, such as nitrogen and caused considerable field adjustments. This is the drift in the zero value that occurs with time and temperature changes. The drift is due to temperature-sensitive electronic circuits and variations in dark currents generated in photomultiplier tubes. For example, photo-multiplier tube dark cuurents are independent of the light coming from the $NO_x$ cells. They wander randomly with time and change rapidly with temperature.

BRIEF DESCRIPTION OF THE PRESENT INVENTION

The present invention avoids or reduces the problems of the prior art, as set forth. For example, the invention overcomes time-lag errors because all three gas readings occur simultaneously under continuous flow conditions.

The present invention also eliminates negative $NO_2$ readings, previously mentioned. Since the invention makes NO and $NO_x$ measurements simultaneously, the $NO_2$ value will always be accurate, positive and free of skew error.

The present invention has also been designed to circumvent the problem of zero-drift. This is done by automatically zeroing the instrument. An optical shutter, in the form of a chopper interrupts the chemiluminescent light coming from the $NO_x$ cells 35 times a second. This produces AC signals having amplitudes equal to the chemiluminescence only. Phase sensitive amplifiers then discard the DC dark currents and amplify the AC signals which are converted to values of NO and $NO_x$ in ppm.

Further, tracking of NO and $NO_x$ channels with time, temperature, line voltage, etc, is insured by having virtually no zero drift, by using a common sample system to the two cells and by operating matched detectors off a common power supply. To further enhance accuracy at fast response, the detectors have a solid state cooling system to reduce random shot noise.

Use in the present invention of dual channels and optical shutters make possible less sophisticated, less expensive and more reliable components than the delicate circuits required for low-level DC measurements.

Several other features are included in the design of the present invention to reduce maintenance time and to improve accuracy. The downstream pump to be explained hereinafter cannot introduce any foreign elements into the system nor can it adversely affect the sample. Filters remove ozone and particulate matter before they reach the pump.

Instantaneous self-tests are incorporated in the design of the present invention. Particularly, light sources in $NO_x$ and NO reaction cells provide a known light level for checking photo-multiplier tube operation, while an induced signal tests the electronics.

Of course, the present invention is directed to apparatus and a method involving chemiluminscent measurements. Although a preferred embodiment of the invention relates to oxides of nitrogen, the invention is applicable to measurements of other compounds of gases able to exhibit chemiluminescence.

BRIEF DESCRIPTION OF THE FIGURES

FIG. 1 is a block diagram of the prior art.

FIG. 2 is a block diagram of the present invention.

FIG. 3 is a plot of the signals emitted from the photo-multiplier tubes, without chopping.

FIG. 4 is a view of an optical shutter or chopper as employed in the present invention.

FIG. 5 is a plot of the output signal from a photo-multiplier tube with AC chopping.

DETAILED DESCRIPTION OF THE INVENTION

Referring to the figures, and more particularly FIG. 1 thereof, a block diagram of the prior art is illustrated. A gas stream which constitutes a sample, and which may include NO and $NO_2$ is introduced at the inlet 9. The sample stream flows through a filter 10 where particulate matter is removed. Filter 10 is fabricated of material which does not interact chemically or in any fashion which may affect the sample composition. Downstream from the filter, the sample is alternately and periodically diverted at 11, through two parallel paths 12 and 13. Path 12 transports the sample directly through pneumatic impedance 17 to a three-way solenoid valve 16. Path 13 transports the sample through a converter 14, pneumatic impedance 19 and to the valve 16. During operation, valve 16 alternately and periodically provides communications between path 12 and tubing 18, and between path 13 and tubing 18. In other words, as sample gas flows through path 12, pneumatic impedance 17 and valve 16 — to tubing 18, there is no sample flow through path 13, converter 14, pneumatic impedance 19, and valve 16 — to tubing 18. During the opposing half of the cycle, as sample gas flows through path 13, converter 14 and valve 16 — to tubing 18, there is no sample flow through path 12. Valve 16 is fabricated from materials which do not interact chemically or in any fashion to effect the sample composition. Valve 16 may be two-position solenoid valve driven electrically. The purpose of converter 14 is to convert the $NO_2$ molecules of the sample to an equivalent amount of NO molecules. Converter 14 can be a low temperature device employing a molybdenum metal surface at 200° to 300°C. By employing the molybdenum surface at this temperature, converter 14 has a conversion efficiency greater than 99 percent, and furthermore will not convert other nitrogen molecules, such as $NH_3$, which may be present in the sample, the NO molecules. Other types of converters and various combinations of these types may be employed, depending upon a particular application.

The outlet from the valve 16 communicates, through tubing 18 to a reaction chamber 20. The reaction chamber 20 will alternately receive the sample gas containing NO and $NO_2$ molecules from path 12 and sample gas containing NO molecules from path 13. The NO molecules from path 13 are equal to the sum of NO and $NO_2$ in the gas sample. From path 13, the $NO_2$ molecules in the gas sample are converted to NO molecules because of the $NO_2$ molecules will not undergo the chemiluminescent reactioon in the reaction chamber, as will the NO. In order to effect the chemiluminescent reaction in the reaction chamber 20, ozone gas is introduced through tubing 25 to reaction chamber 20. Ozone gas is produced from air flowing through inlet 22, dryer 24, and ozone generator 26. The purpose of the dryer 24 is to dry the air by means of a desiccant, such as anhydrous calcium sulphate. Air from dryer 24 is transmitted to an ozone generator 26 which produces ozone by acting on the oxygen in the air. Typically, such a generator will be of the discharge type. The air stream containing ozone is transported through pneumatic impedance 21, tube 25 and is introduced to the reaction chamber 20 where the ozone is mixed with the sample air stream transported through path 12, valve 16, pneumatic impedance 17 and tubing 18. The ozone is then mixed with the sample stream transported through path 13, converter 14, pneumatic impedance 19, and tubing 18. As the sample air and air containing ozone are mixed in the reaction chamber 20, the NO molecules contained in the air sample and the ozone contained in the dry air stream chemically react and produce a chemiluminescent radiation of an intensity which is proportional to the NO concentration in the sample air stream. The chemiluminescent reaction between NO and $O_3$ is well known.

Reaction chamber 20 is provided with a window 28 to permit the chemiluminescent radiation, produced by the reaction to be emitted from reaction chamber 20. The intensity of the radiation is measured by photomultiplier tube 30 which is positioned adjacent to window 28. Reaction chamber 20, window 28, and photomultiplier tube 30 are secured together in a fashion by which stray light does not enter photomultiplier tube 30. The only light which enters photo-multiplier tube 30 arises from the chemiluminescent radiation produced by the reaction between NO and $O_3$. The intensity of chemiluminescent radiation may be measured at the output 32 of photomultiplier tube 30.

The resultant gas mixture flows from the reaction chamber 20 through exhaust tube 61, exhaust filter 52, vacuum regulator 53, vacuum pump 156, and is ejected from the system through an exhaust port 158. Exhaust filter 52 is typically a cartridge containing activated charcoal which converts $O_3$ to $O_2$ and otherwise prevents the existence of $O_3$ downstream. Vacuum regulator 53 maintains a constant vacuum pressure in reaction chamber 20. By this action the reactions between NO and $O_3$, the gas flow rates through paths 12, 13 and 25, to reaction chamber 29 are set and controlled.

As shown by FIG. 1, photomultiplier tube output 32 is electronically connected to the NO sample and hold circuit 34 which directly samples photomultiplier tube output 32 only during the half-cycle when the sample gas is flowing through path 12, pneumatic impedance 17, valve 16, and tubing 18 — to reaction chamber 20. At the end of this half-cycle, the level of output 32 is held by NO sample and hold circuit 34 for further processing. Photomultiplier tube output 32 is electronically connected to the $NO_x$ sample and hold circuit 38 which directly samples output 32, only during the half-cycle where the sample gas is flowing through path 13, converter 14, pneumatic impedance 19, valve 16, and tubing 18-to reaction chamber 20. At the end of the second half-cycle, the level output 32 is held by $NO_x$ sample and hold circuit 38 for further processing. At the end of the full cycle, NO sample and hold circuit 34 releases and holds the most recent level in the cycle of output 32 to the NO amplifier 40, and to differemtial amplifier 36. Simultaneously, $NO_x$ sample and hold circuit 38 releases and holds the most recent level in the cycle of output 32 to $NO_x$ amplifier 44 and to differential amplifer 36. Thus, the signals from output amplifiers 40 and 44 are proportional to the NO and $NO_x$ concentration levels respectively in the sample gas. Differential amplifier 36 performs the function of subtracting the output of the NO sample and hold circuit 34 from the signal of the $NO_x$ sample and hold circuit 38. The differential amplifier output 50 is by definition proportional to the $NO_2$ level in the sample gas. Differential amplifier output 50 is further processed by $NO_2$ output amplifier 42. Thus, the output of $NO_2$ output amplifier 42 is proportional to the $NO_2$ concentration level in the sample gas.

The sequence and synchronization of events of valve 16, NO sample and hold circuit 34, and $NO_x$ sample and hold circuit 38 is controlled and and established by a programmer 157.

FIG. 2 indicates a block diagram of the present invention which is a marked improvement over the prior art of FIG. 1. The basic operating principle and a number of components in FIG. 2 are identical to that of the prior art (FIG. 1). However, the system or combination or arrangement of components present vastly contrasting designs.

It is to be emphasized that the present invention, both as to the aspects and method, is not directed to the chemistry of chemiluminescence, which is well established in the prior art. Thus, although the present invention may be utilized in the analysis of various compounds of gases, which may be made to undergo chemiluminescence, the following preferred embodiment of the present invention will relate to oxides of nitrogen. However, since the chemistry, per se, is not novel, the preferred embodiment relating to oxides of nitrogen is to be considered exemplary or illustrative, only.

Referring to the diagram of FIG. 2, the gas sample is introduced at inlet 54. An in-line filter 55 is provided to remove particulate matter. Filter 55 is fabricated of materials which do not interact chemically or in any fashion which may affect the sample composition. After traversing filter 55, the gas sample is continuously diverted into path 56 and path 66.

Path 56 transports the sample gas through pneumatic impedance 57 and directly to reaction chamber 58. Path 66 transports the sample gas through converter 68 and pneumatic impedance 61 to reaction chamber 70. The purpose of converter 68 is identical to that of converter 14 of FIG. 1. The purposes of pneumatic impedance 57 and 61 are identical to those of pneumatic impedance 17 and 19 of FIG. 1. The purposes of reaction chamber 58 and reaction chamber 70 are identical to those of reaction chamber 20 of FIG. 1.

Ozone gas is supplied to reaction chamber 58 and reaction chamber 70 from air oxygen passing through inlet 78, air dryer 80, ozone generator 82 and penumatic impedances 85 and 87. The magnitudes of pneumatic impedances 85 and 87 are set to split evenly the ozone flow rates between reaction chambers 58 and 70. The magnitudes of pneumatic impedances 57 and 61 are set to split evenly the gas sample flow rates entering inlet 54 between reaction chambers 58 and 70. Although not shown by FIG. 2, the pneumatic impedances 61, 57, 85 and 87 can be temperature controlled to provide a constant pneumatic impedance over large ambient and surrounding temperature variations. Since the chemiluminescent radiation intensity is proportional to the gas flow rates into the reaction chambers 58 and 70, temperature control of pneumatic impedances 61, 57, 85 and 87 will enhance the stability of outputs 106, 116 and 108 thus providing a more accurate analysis of the sample gas.

At this stage it is noted that in comparing the networks of FIG. 1 and FIG. 2 that valve 16 of FIG. 1 is not present in FIG. 2. Also, two reaction chambers 58 and 70 are utilized in the present invention where one is used in the prior art. The network of FIG. 2, unlike the network of FIG. 1, permits the continuous flow of sample gas through path 56 and path 66 to reaction chambers 58 and 70, respectively.

NO and $NO_2$ molecules contained by the sample gas are introduced through path 56 to reaction chamber 58 where only the NO molecules undergo a reaction with ozone, as prescribed in the prior art. The upper path 56 accomplishes measurement of NO in the air sample. $NO_x$ measurements are accomplished in path 66 through a conversion of the $NO_2$ molecules to an equivalent number of NO molecules by converter 68 in addition to the NO present in the same. Converter 68 may be a catalytic converter as in the prior art. The reactions between NO and $O_3$ in reaction chambers 58 and 70 produce a chemiluminescent radiation having intensities which are proportional to the NO molecules contained in the sample gas flowing through path 56, and the NO and converted $NO_2$ molecules contained in the sample gas flowing through path 66, respectively.

Referring to the upper path 56, the reaction chamber 58 has a window 60 formed therein, as in the case of the previously explained prior art. Also, a photo-multiplier tube 64 is provided for measuring the chemiluminescent intensity in the reaction chamber 58. Similar components are included for the path 66 and are respectively indicated at 70, 72 and 76.

In marked distinction from the DC readout at the output of the photo-multiplier tube of FIG. 1, AC signals are produced in the embodiment of FIG. 2, due to the introduction of optical shutters at 62 and 74. A typical type of shutter may be a light chopper, to be discussed in greater detail hereinafter. However, suffice it to say that use of optical shutters present a reliable AC signal at the photo-multiplier tube outputs, for subsequent measurement.

The same basic exhaust system is utilized in FIG. 2 as in FIG. 1. The reaction chambers 58 and 70 have respective outlet lines 88 and 90 that communicate with a central exhaust line 92. From there, the exhausted gas is filtered at 94 and passes through interconnected vacuum regulator 96 and vacuum pump 98. The outlet 100 indicates final exhaust. The regulator 96 ensures that the chambers 58 and 70 maintain preselected pressures.

It must be stressed at this point that the prior art requires the alternate flow of sample gas, accomplished by valve 16, through path 12 and path 13 containing coverter 14. This is in marked contrast to FIG. 2 (the invention) which includes dual channels of gas flow 56, 66. The dual channels are of course continuous through the photo-multiplier tubes. Rather than utilizing the necessary sample and hold circuits of FIG. 1, the present invention merely connects amplifiers 102 and 104 to the outputs of the photo-multiplier tubes 64 and 76. The output 106 of amplifier 102 is proportional to the NO concentration level of the sample gas entering at 54. The output 108 from amplifier 104 is proportional to the $NO_x$ concentration level, which by definition is the sum of the NO and $NO_2$ concentration levels of the gas sample entering at 54.

As in the case of the prior art, differential amplifier 114 has its inputs 110 and 112 connected to the outputs of the amplifiers 104 and 102. Differential amplifier 114 performs the function of subtracting the output 106 of amplifier 102 from the output 108 of amplifier 104. Output 116 of differential amplifier 114 is proportional to the $NO_2$ concentration level of the sample gas entering at 54. Again, it must be emphasized that the output electronics operate on a continuous basis rather than requiring switching as in the case of 57 (FIG. 1).

Regarding individual components, the photo-multiplier tubes, used in the invention, may be of the type manufactured by Hamamatsu and known as model 374. It is important that the windows 60 and 72 permit the passage of light only above 6,000 A. The vacuum regulator 96 may be of the type manufactured by Fairchild and the pump 98 may be of the type manufacuted by Thomas Industries and denoted by model 2107CA18. With the described embodiment, the pressure at exhaust 100 will be about −18 inches Hg., at 600cc/min. Regarding the ozone generator it may typically include two electrodes maintained at 9–15KV pp and 3–5KV rms. The concentration levels from the ozone generator 82 are typically 1000–6000 ppm at a flow rate of 100cc/min.

FIG. 3 illustrates the component signals that manifest themselves at the output of photo-multiplier tube 30. Plot 118 shows a composite of the dark current and noise 120, generated by the photomultiplier tube 30. The output of photomultiplier tube 30 is proportional to the NO concentration level of the gas sample. Output 122 is a composite of 118 and the signal generated by the chemiluminescent radiation in the reaction chamber 20.

By mounting the photomultiplier tubes 64 and 76 in a cool surrounding, the noise level may be substantially reduced. This action permits the measurement of lower NO and $NO_x$ concentration levels of gas samples. Therefore, the sensitivity of the analyzer is enhanced.

FIG. 4 illustrates a typical optical shutter or light chopper such as diagramatically indicated by 62 and 74 (FIG. 2). The shutter is generally indicated by reference numeral 124 and is seen to include a circular circumference 126. A number of opaque blades 128 are formed in the body of the circular chopper. In between the opaque sections or blades are transparent sections 130. When an opaque section is interposed between the windows 60, 72 and respective photo-multiplier tubes 64, 76, the light from chemiluminescence is prevented from being detected because it impinges, as shown at 129, on the opaque section. During this period, the output at 106, 108, and 116 will generally resemble the lower portion of FIG. 5. As will be seen, the dark current level 132 will be read at these outputs. When the light is permitted to pass through the transparent sections of the chopper 124, as shown by 131, a strong signal level at 134 will make itself evident. By measuring the indicated signal amplitude, a measurement of the various nitrogen oxide gases may be made. It is important for the frequency of chopper operation to be rapid enough so that the dark current levels 132 and 136 have not undergone a change, and are the same. This permits for a constant signal amplitude to be measured during the sampling time interval.

As will be appreciated from a review of the invention, marked advantages are obtained with the present system as compared with the prior art.

As seen in FIG. 2, the invention may include a self-testing feature. Lamps 59 and 75 are respectfully positioned within the reaction chambers 58 and 70. Upon energization of these lamps, known light emission will occur to cause a readout of predetermined values at the outputs 106, 116, 108. This serves as a means for checking the system from the reaction chambers through the signal outputs.

Of course, the present invention is directed to apparatus and a method involving chemiluminescent measurements. Although a preferred embodiment of the invention relates to oxides of nitrogen, the invention is applicable to measurements of other compounds of gases able to exhibit chemiluminescence. It is understood, that if compounds other than oxides of nitrogen are to undergo analysis by the present method and apparatus, a reactant other than ozone may be required, for introduction in the reaction chambers. The choice of a reactant depends upon the particular compound undergoing analysis and is not within the purview of the present invention to claim any novel chemistry, per se.

It should be understood that the invention is not limited to the exact details of construction shown and described herein for obvious modifications will occur to persons skilled in the art.

What is claimed is:

1. A system for measuring NO, $NO_2$ and $NO_x$ concentrations in a gas mixture sample where $NO_x = NO + NO_2$, the system having dual path channels and comprising:
    means located in a first path for continuously obtaining and transferring a first portion of the sample to a first reaction chamber;
    means communicating with the first path for continuously introducing ozone into the reaction chamber for reaction with the NO in the first sample portion to cause chemiluminescence;
    means located in a second path for simultaneously obtaining a second portion of the sample and for continuously converting the $NO_2$ in the second portion of the sample to NO;
    means located in the second path for continuously transferring the converted second sample portion to a second reaction chamber;
    means communicating with the second path for continuously introducing ozone into the second reaction chamber for reaction with the NO therein, thus causing chemiluminescence; and
    means for detecting the light from the chemiluminescence in the respective reaction chambers for measuring signals indicative of NO and $NO_x$ in the sample portions.

2. The subject matter of claim 1 together with optical shutter means respectively located between the reaction chambers and their detecting means to chop light emitted from the reaction chambers, thus causing the detection of respective AC signals.

3. The subject matter of claim 1 wherein first detection means provides a continuous measure of NO in the first sample portion through the first path and wherein second detection means provides a continuous measure of $NO_x$ in the second sample portion passing through the second path; and
    means for subtracting outputs from the first and second detection means for producing a signal which measures the $NO_2$ portion of the sample.

4. The subject matter of claim 2 wherein first detection means provides a continuous measure of NO in the first sample portion through the first path and wherein the second detection means provides a continuous measure of $NO_x$ in the second sample portion passing through the second path; and
    means for subtracting outputs from the first and second detection means for producing a signal which measures the $NO_2$ portion of the sample.

5. The subject matter of claim 4 together with test lamp sources located in the respective chambers for emitting a predetermined light output from the chambers.

6. The subject matter as defined in claim 4 wherein the transferring means in the first path comprises means located at the inlet of the first path reaction chamber for delaying the passage of the first sample portion therethrough, thus synchronizing sample flow through the first and second paths.

7. An analyzer having plural channels for use in measuring compounds of a preselected gas, the analyzer comprising:
    means located in a first path for continuously transferring a first portion of inlet gas sample, including the preselected gas, to a first reaction chamber;
    means communicating with the first path for continuously introducing a reactant into the reaction chamber for reacting with a first compound of the preselected first sampled gas portion to cause chemiluminescence;
    converting means located in a second path for simultaneously and continuously converting a second compound of a second portion of the preselected sampled gas to the first compound;
    means located in the second path for continuously transferring the converted second portion of the sampled gas to a second reaction chamber;
    means located in the second path for continuously introducing the reactant into the second reaction chamber for reacting with the first compound therein, thus causing chemiluminescence;
    means for respectively detecting the light from chemiluminescence in the reaction chambers; and
    means for venting the reaction chambers.

8. A method for measuring NO and NO$_2$ in a gas mixture sample, the method comprising the following steps:
- continuously introducing the sample along two parallel paths;
- continuously reacting the sample, along a first path, with a preselected reactant for causing chemiluminescence of NO in the sample;
- continuously converting, along the second path, NO$_2$ in the sample to NO;
- continuously reacting, along the second path, the NO with the reactant to cause chemiluminescence of the NO;
- continuously measuring the light emission from the first and second path chmeiluminescence for determining the concentrations, in the mixture, of NO and NO$_x$, where NO$_x$ × NO + NO$_2$.

9. A method for measuring first and second compounds in a gas mixture sample, the method comprising the following steps:
- continuously introducing the sample along two parallel paths;
- continuously reacting the sample, along a first path, with a preselected reactant for causing chemiluminescence of the first compound in the sample;
- continuously converting, along the second path, the second compound in the sample to the first compound;
- continuously reacting, along the second path, the first compound with the reactant to cause chemiluminescence of the first compound;
- continuously measuring the light emission from the first and second path chemiluminescence for determining the concentrations, in the mixture, of the first and second compounds.

10. The subject matter of claim 2 together with test lamp sources located in the respective chambers for emitting a predetermined light output from the chamber.

* * * * *